United States Patent
Karube

(10) Patent No.: US 11,718,755 B2
(45) Date of Patent: Aug. 8, 2023

(54) ELASTOMER COMPOSITION AND MEDICAL CONTAINER STOPPER FORMED BY MOLDING SAME

(71) Applicant: MCPP Innovation LLC, Tokyo (JP)

(72) Inventor: Kanae Karube, Mie (JP)

(73) Assignee: MCPP Innovation LLC, Tokyo (JP)

( * ) Notice: Subject to any disclaimer, the term of this patent is extended or adjusted under 35 U.S.C. 154(b) by 209 days.

(21) Appl. No.: 16/983,135

(22) Filed: Aug. 3, 2020

(65) Prior Publication Data

US 2020/0362170 A1 Nov. 19, 2020

Related U.S. Application Data

(63) Continuation of application No. 16/120,650, filed on Sep. 4, 2018, now abandoned, which is a continuation
(Continued)

(30) Foreign Application Priority Data

Mar. 3, 2016 (JP) .................................. 2016-041123

(51) Int. Cl.
*C08L 91/00* (2006.01)
*A61L 29/04* (2006.01)
(Continued)

(52) U.S. Cl.
CPC ............ *C08L 91/00* (2013.01); *A61J 1/1406* (2013.01); *A61L 29/04* (2013.01); *C08L 51/06* (2013.01);
(Continued)

(58) Field of Classification Search
CPC ........ C08L 53/02; C08L 53/025; C08L 91/00; C08L 51/06; A61J 1/14
See application file for complete search history.

(56) References Cited

U.S. PATENT DOCUMENTS 3,584,883 A 6/1971 Sheets
4,975,308 A 12/1990 Bayan
(Continued)

FOREIGN PATENT DOCUMENTS

CN 102549054 A 7/2012
CN 104893315 A 9/2015
(Continued)

OTHER PUBLICATIONS

Machine translation of JP 2015205965 (2015, 8 pages).*
(Continued)

*Primary Examiner* — Brieann R Johnston
(74) *Attorney, Agent, or Firm* — Oblon, McClelland, Maier & Neustadt, L.L.P.

(57) ABSTRACT

The elastomer composition of the present invention comprises a thermoplastic elastomer composition which contains 20 to 80% by weight of component (A), 1 to 25% by weight of component (B), and 1 to 70% by weight of component (C): Component (A): at least one block copolymer selected from: a block copolymer having a polymer block derived from a vinyl aromatic compound and a polymer block derived from at least one selected from a conjugated diene and isobutylene; and a block copolymer obtained by hydrogenating the block copolymer; Component (B): a polypropylene resin containing component (B1): a modified polypropylene obtained by graft-modifying a polypropylene resin with a diene compound; and Component (C): a hydrocarbon softener for rubber.

15 Claims, 1 Drawing Sheet

Related U.S. Application Data of application No. PCT/JP2017/008511, filed on Mar. 3, 2017.

(51) Int. Cl.
  *C08L 53/02* (2006.01)
  *C08L 51/06* (2006.01)
  *A61J 1/14* (2023.01)

(52) U.S. Cl.
  CPC .......... *C08L 53/02* (2013.01); *C08L 2205/03* (2013.01); *C08L 2207/04* (2013.01)

(56) References Cited

U.S. PATENT DOCUMENTS

| | | | |
|---|---|---|---|
| 2005/0143510 A1* | 6/2005 | Nakayama | C08F 297/08 524/495 |
| 2009/0269590 A1 | 10/2009 | Furukawa | |
| 2012/0059108 A1 | 3/2012 | Date | |
| 2012/0181295 A1 | 7/2012 | Sasaki | |
| 2013/0116648 A1 | 5/2013 | Muto | |
| 2013/0231433 A1 | 9/2013 | Date | |

FOREIGN PATENT DOCUMENTS

| | | | |
|---|---|---|---|
| EP | 2 484 723 A1 | 8/2012 | |
| EP | 3 133 121 A1 | 2/2017 | |
| JP | 61-037242 | 2/1986 | |
| JP | 7-228749 | 8/1995 | |
| JP | 9-000601 | 1/1997 | |
| JP | 2006-291019 | 10/2006 | |
| JP | 2007-050138 | 3/2007 | |
| JP | 2010-227285 | 10/2010 | |
| JP | 2012-25944 | 2/2012 | |
| JP | 2013-074596 | 4/2013 | |
| JP | 2014088475 A | * | 5/2014 |
| JP | 2015-019750 | 2/2015 | |
| JP | 2015-98542 A | 5/2015 | |
| JP | 2015205965 A | * | 11/2015 |
| WO | 2008139512 | 11/2008 | |
| WO | WO 2010/103988 | 9/2010 | |
| WO | WO 2011-135927 | 11/2011 | |
| WO | WO 2011/162257 | 12/2011 | |
| WO | WO 20016/159912 A1 | 10/2015 | |

OTHER PUBLICATIONS

Machine translation of JP 2014-088475 (2014, 3 pages).*
Japanese Office Action dated Dec. 1, 2020 in Japanese Patent Application No. 2018-503425 (with English translation), 5 pages.
International Search Reprot issued on in International Application No. PCT/JP2017/008511, dated May 9, 2017.
Extended European Search Report dated Mar. 18, 2019 in the corresponding European Patent Application No. 17760176.2 5 pages.
Machine translated equivalent of WO 2008-139512 (2008, 6 pages). A human translation has been requested.
Machine translated English language equivalent of JP Application 2013-239108, Which is the same as JP Publication 2015/098542 (2015, 15 pages).
Combined Chinese Office Action and Search Report dated Aug. 24, 2020 in Patent Application No. 201780014815.7 (with English language translation), 13 pages.

* cited by examiner

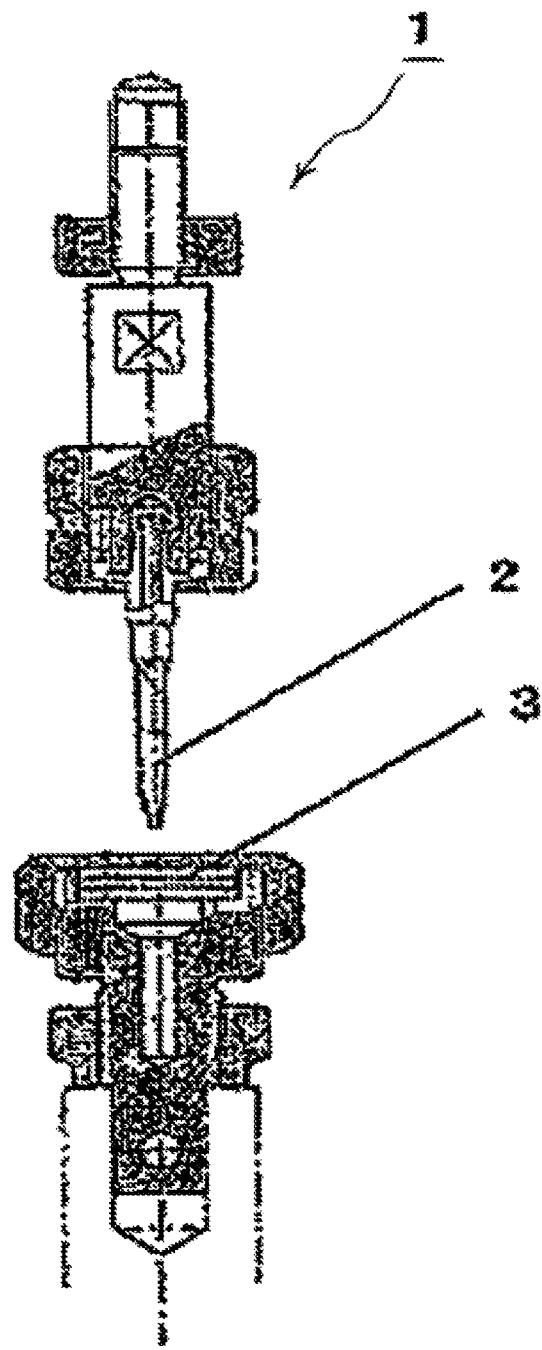

ELASTOMER COMPOSITION AND MEDICAL CONTAINER STOPPER FORMED BY MOLDING SAME

TECHNICAL FIELD

The present invention relates to an elastomer composition, and more specifically relates to an elastomer composition for forming a medical stopper which has small compression set and is good in softness, liquid leakage sealing properties, needle sticking properties, sterilization stability, molding processability, and the like, and a medical stopper formed by molding the elastomer composition.

BACKGROUND ART

A transfusion bag means a container used when a liquid such as a blood preparation or an intravenous injection liquid is injected into a living body, or when they are stored. Currently, a glass, a plastic, or the like is used for the transfusion bag, and a rubber stopper is fitted into an opening portion of the container so that a liquid (content liquid) filled therein does not leak. When the transfusion bag is used, an injection needle such as a metal needle or a plastic needle is pierced into the rubber stopper, and the content liquid is generally taken out therethrough.

In use of the transfusion bag described above, the injection needle is plucked from the rubber stopper at the time of treatment, and the injection needle is plucked not only after the content liquid has been completely consumed, but may also in a state where the content liquid remains in the transfusion bag. At this time, properties required for the rubber stopper is liquid leakage sealing properties. In a case where the sealing properties are insufficient, the content liquid may leak or disperse from a hole formed in a position where the injection needle is pierced.

Conventionally, in a medical member such as the rubber stopper for the transfusion bag, vulcanized rubber such as isoprene rubber excellent in a liquid leakage sealing property is often used, but the vulcanized rubber contains an additive which is not suitable for medical supplies and is inferior in molding processability. In addition, when a main material of the transfusion bag changes from glass to plastic, attempts have been made to use a rubber stopper made of a thermoplastic elastomer because the transfusion, bag body made of plastic can be fused and fitted by two-color molding.

Among them, a styrene thermoplastic elastomer is considered as a material most expected to substitute for the vulcanized rubber because of excellent rubber elasticity, and it is disclosed that the styrene elastomer having a specific hardness range is excellent in balance of liquid leakage sealing properties, piercing strength and handling properties (see Patent Document 1,). In addition, it is disclosed that a medical rubber stopper having a specific molecular weight distribution and containing a styrene thermoplastic elastomer, a hydrocarbon softener for rubber, and a polyolefin resin exhibits excellent needle sticking properties (see Patent Document 2.). Further, a technique of adding the vulcanized rubber to the styrene thermoplastic elastomer is also disclosed (see Patent Document 3.).

BACKGROUND ART DOCUMENT

Patent Document

Patent Document 1: JP-A-H07-228749
Patent Document 2: JP-A-2012-025944
Patent Document 3: JP-A-2010-227285

SUMMARY OF THE INVENTION

Problems to be Solved by the Invention

According to detailed consideration of the inventors, it has been found that a molded body obtained by molding a thermoplastic elastomer composition as described in the above Patent Documents 1 to 3 does not completely satisfy all of compression set, liquid leakage sealing properties, needle sticking properties, sterilization stability, and molding processability which is performance required for a stopper provided in a medical container.

A problem of the present invention is to solve the above problems. Namely, a problem of the present invention is to provide an elastomer composition for forming a medical container stopper excellent in softness, liquid leakage sealing properties, needle sticking, properties, sterilization stability, molding processability, and the like, and a medical container stopper formed by molding the elastomer composition.

Means for Solving the Problems

As a result of earnest consideration to solve the above problems, a modified polypropylene resin having a specific structure is used, and an elastomer composition containing a thermoplastic elastomer composition containing a specific amount of a block copolymer and a hydrocarbon softener for rubber is used, so that the inventors have found that the medical container stopper formed by molding the elastomer composition has high performance and all the conventional problems can be solved. The present invention has been accomplished based on these findings.

Namely, a gist of the present invention is as the following [1] to [9].

[1] A elastomer composition containing a thermoplastic elastomer composition containing 20 to 80% by weight of component (A), 1 to 25% by weight of component (B), and 1 to 70% by weight of component (C) with respect to a total amount of the following component (A), component (B), and component (C):

Component (A): at least one block copolymer selected from: a block copolymer having a polymer block derived from a vinyl aromatic compound and a polymer block derived from at least one selected from a conjugated diene and isobutylene; and a block copolymer obtained by hydrogenating the block copolymer;

Component (B): a polypropylene resin containing component (B1) below

Component (B1): a modified polypropylene obtained by graft-modifying a polypropylene resin with a diene compound; and Component (C): a hydrocarbon softener for rubber.

[2] The elastomer composition according to the above [1], wherein the diene compound of the component (B1) is a conjugated diene compound.

[3] The elastomer composition according to the above [2], wherein the conjugated diene compound of the component (B1) is isoprene.

[4] The elastomer composition according to any one of the above [1] to [3], wherein the component (B1) has a melt flow rate (ISO 1133 (230° C., load 2.16 kg)) of 0.1 to 200 g/10 min.

[5] The elastomer composition according to any one of the above [1] to [4], wherein a weight average molecular weight (Mw) of the component (A) is 100,000 to 500,000.

[6] The elastomer composition according to any one of the above [1] to [5], wherein the elastomer composition has durometer hardness A (ISO 7619-1) of 10 to 40.

[7] The elastomer composition according to any one of the above [1] to [6], wherein the elastomer composition is an elastomer composition for a medical container stopper.

[8] A medical container stopper formed from the elastomer composition according to any one of the above [1] to [7].

[9] The medical container stopper according to the above [8], wherein the medical container stopper is a medical rubber stopper.

Effect of the Invention

According to the elastomer composition of the present invention, it is possible to mold a medical member such as a medical container stopper which has small compression set and is excellent in softness, liquid leakage sealing properties, needle sticking properties, sterilization stability, molding processability, and the like. Having the above effect, the elastomer composition of the present invention can be suitably used for a medical container stopper such as a medical rubber stopper, a medical cap, a medical gasket, a medical packing, a catheter tube, a resuscitator, and the like.

BRIEF DESCRIPTION OF DRAWINGS

FIG. 1 is a cross-sectional view of a jig for evaluating needle sticking properties used in Examples.

DETAILED DESCRIPTION OF EMBODIMENTS

Although embodiments of the present invention will be described in detail below, the following description is an example of embodiments of the present invention, and the present invention is not limited to the following description unless the present invention exceeds the gist. In the present specification, in a case where an expression "to" is used, it is used as an expression including a numerical value or a physical property value before and after the expression.

[Elastomer Composition]

The elastomer composition of the present invention contains the following component (A), component (B), and component (C), and contains a thermoplastic elastomer composition (hereinafter may be referred to as "thermoplastic elastomer composition of the present invention") containing 20 to 80% by weight of component (A), 1 to 25% by weight of component (B), and 1 to 70% by weight of component (C).

Component (A): at least one block copolymer selected from: a block copolymer having a polymer block derived from a vinyl aromatic compound and a polymer block derived from at least one selected from a conjugated diene and isobutylene; and a block copolymer obtained by hydrogenating the block copolymer Component (B): a polypropylene resin containing component (B1) below Component (B1): a modified polypropylene obtained by graft-modifying a polypropylene resin with a diene compound Component (C): Hydrocarbon Softener for rubber <Component (A)>

In the present invention, component (A) is at least one block copolymer selected from a group consisting of a block copolymer having a polymer block (hereinafter may be referred to as "block P") derived from a vinyl aromatic compound and a polymer block derived from at least one selected from a conjugated diene and isobutylene (hereinafter referred to as "block Q") and a block copolymer formed by hydrogenating the block copolymer.

Although the vinyl aromatic compound of a monomer constituting the block P is not particularly limited, a styrene derivative such as styrene or α-methylstyrene is preferable. Among them, styrene is preferably used as a main constituent. The block P may contain a monomer other than the vinyl aromatic compound as a raw material. Here, in the present invention, "as a main constituent" means 50% by weight or more.

Examples of the monomer other than the vinyl aromatic compound include ethylene, α-olefins, and the like. In a case where the block P contains the monomer other than the vinyl aromatic compound as a raw material, a content of the monomer is less than 50% by weight, and preferably 40% by weight or less. The content of the monomer other than the vinyl aromatic compound is in this range, so that heat resistance and compression set tend to be good.

The block Q is derived from a conjugated diene and/or isobutylene. Although the conjugated diene of a monomer that can be used in the block Q is not particularly limited, preferably butadiene and/or isoprene, and more preferably butadiene and isoprene are used as main constituents. The block Q may contain a monomer other than the conjugated diene as a raw material.

Examples of the monomer other than the conjugated diene and/or isobutylene include styrene and the like. In a case where the block Q contains the monomer other than the conjugated diene and/or isobutylene as a raw material, a content of the monomer is less than 50% by weight, and preferably 40% by weight or less. The content of the monomer other than the conjugated diene and or, isobutylene is in this range, so that bleed-out tends to be suppressed.

The block copolymer of component (A) may be a hydrogenated block copolymer obtained by hydrogenating a block copolymer having the block P and the block Q, and more specifically, may be a hydrogenated block copolymer obtained by hydrogenating a double bond of the block Q of the block copolymer. In the block copolymer of component (A), the number of block P and block Q is not particularly limited, but preferably includes at least two blocks P and at least one block Q. A hydrogenation rate of the block Q is not particularly limited, but is preferably from 80 to 100% by weight, and more preferably from 90 to 100% by weight. The block Q is hydrogenated in the above range, so that there is a tendency that adhesive properties of the obtained thermoplastic elastomer composition decrease; elastic properties increase; and a decrease in physical properties during sterilization is suppressed. The hydrogenation ratio can be measured by a $^{13}C$-NMR.

In a case where the conjugated diene of the monomer composing the block Q is butadiene, butadiene in the microstructure can take a 1,4-additional structure and a 1,2-additional structure, but in particular, in a case where the block Q is a hydrogenated derivative and is mainly composed of butadiene, the 1,4-additional structure of butadiene in the microstructure of the block Q is preferably from 20 to 100% by weight.

In a case where the conjugated diene of the monomer composing the block is isoprene, the isoprene in the microstructure can take a 1,2-additional structure, a 1,4-additional structure, and a 3,4-additional structure, and similarly to the above, in particular, in a case where the block Q is a hydrogenated derivative and is composed of isoprene, the 1,4-additional structure of isoprene in the microstructure of the block Q is preferably from 30 to 100% by weight.

In a case where the block Q is a hydrogenated derivative and the conjugated diene of the monomer constituting the block Q contains butadiene and isoprene, the 1,4-additional structure of butadiene and isoprene in the microstructure of the block Q are preferably from 20 to 100% by weight and from 30 to 100% by weight.

In any case, by setting a ratio of the 1,4-additional structure to the above range, the adhesive properties of the obtained thermoplastic elastomer composition tend to decrease and the elastic properties tend to increase. The ratio of the 1,4-additional structure (hereinafter, sometimes referred to as "1,4-microstructure ratio") can be measured by $^{13}$C-NMR.

Component (A) in the present invention is not particularly limited as long as it has a structure including the block P and the block Q, and may be any of linear, branched, radial, and the like, but is preferably a block copolymer represented by the following formula (1) or (2). Further, the block copolymer represented by the following formula (1) or (2) is more preferably a hydrogenated block copolymer obtained by hydrogenation. When the copolymer represented by the following formula (1) or (2) is a hydrogenated block copolymer, thermal stability is good.

   (1)

   (2)

(In the formula, P represents the block P, Q represents the block Q, m represents an integer of 1 to 5, and n represents an integer of 2 to 5.)

In the formula (1) or (2), it is preferable that m and n are large in decreasing an order-disorder transition temperature as a rubbery polymer, while it is preferable that they are small in ease of manufacturing and cost.

In a case where component (A) is a hydrogenated block copolymer represented by the formula (1) or (2) and the block Q is composed of butadiene, the 1,4-additional structure of butadiene in a microstructure of the block Q is preferably from 20 to 100% by weight. Similarly, in a case where the block Q is composed of isoprene, the 1,4-additional structure of isoprene in the microstructure of the block Q is preferably from 30 to 100% by weight. Similarly, in a case where the block Q is composed of butadiene and isoprene, the 1,4-additional structures of butadiene and isoprene in the microstructure of the block Q are preferably from 20 to 100% by weight and from 30 to 100 by weight, respectively.

In any case, by setting the 1,4-microstructure ratio to the above range, the adhesive properties of the obtained thermoplastic elastomer composition tend to decrease and the elastic properties tend to increase.

As the block copolymer and/or the hydrogenated block copolymer (hereinafter may be referred to as "(hydrogenated) block copolymer"), due to excellent rubber elasticity, the (hydrogenated) block copolymer represented by the formula (1) is rather preferable than the (hydrogenated) block copolymer represented by the formula (2); the (hydrogenated) block copolymer represented by the formula (1) in which m is 3 or less is more preferable; the (hydrogenated) block copolymer represented by the formula (1) in which m is 2 or less is further preferable; and the (hydrogenated) block copolymer represented by the formula (1) in which m is 1 is most preferable.

Although weight proportions of the block P and the block Q constituting component (A) are arbitrary, it is preferable that the block P is many in terms of the mechanical strength and the thermal fusion strength of the thermoplastic elastomer composition used in the present invention, and it is preferable that the block P is few in terms of softness, profile extrusion moldability, and bleed-out suppression.

The weight proportion of the block P in the component (A) is preferably 10% by weight or more; more preferably 15% by weight or more; and still more preferably 20% by weight or more, and preferably 80% by weight, or less; more preferably 75% weight or less; and still more preferably 70% by weight or less.

The method for producing component (A) in the present invention may be any method as long as the above structure and physical properties are obtained, and is not particularly limited. Specifically, for example, a lithium catalyst or the like is used by a method described in JP-B-S40-23798, and can be obtained by performing block polymerization in an inert solvent. The hydrogenation of the block copolymer can be performed in the presence of a hydrogenation catalyst in an inert solvent by a method described in JP-B-S42-8704, JP-B-S43-6636, JP-A-S59-133203, JP-A-S60-79005, for example. In the hydrogenation treatment, it is preferable that 50% or more of an olefinic double bond in the polymer block is hydrogenated; more preferable that 80% or more is hydrogenated, and it is preferable that 25% or less of an aromatic unsaturated bond in the polymer block is hydrogenated.

Examples of commercially available products of such hydrogenated block copolymer include "Kraton (registered trademark)-G' series" and "Kraton (registered trademark)-A series" manufactured by Kraton Polymer Corporation, "Septon (registered trademark) series" and a part of grade of "Hybrar (registered trademark) series" manufactured by Kuraray Corporation, "Tuftec (registered trademark) series" manufactured by Asahi Kasei Corporation, and the like. Examples of commercially available products of the non-hydrogenated block copolymer include "Kraton (registered trademark)-D series" manufactured by Kraton Polymer Corporation, a part of grade of "Hybrar (registered trademark) series" manufactured by Kuraray Corporation, "Tufprene (registered trademark) series" manufactured by Asahi Kasei Corporation, and the like. Among these, the corresponding product can be appropriately selected and used.

The number average molecular weight (Mn) of component (A) in the present invention is not particularly limited, but is preferably 90,000 or more, more preferably 140,000 or more, and still more preferably 180,000 or more, and preferably 450,000 or less, more preferably 410,000 or less, and still more preferably 360,000 or less. When the number average molecular weight of component (A) is within the above range, moldability and heat resistance tend to be good.

Although the weight average molecular weight (Mw) of component (A) is not particularly limited, it is preferably in a range of 100,000-500,000. Namely, the weight average molecular weight is preferably 100,000 or more; more preferably 150,000 or more; and still more preferably 200, 000 or more, and preferably 500,000 or less; more preferably 450,000 or less; and still more preferably 400,000 or less. When the weight average molecular weight of component (A) is within the above range, moldability and heat resistance tend to be good.

In the present invention, the weight average molecular weight (Mw) and the number average molecular weight (Mn) of component (A) are polystyrene equivalent values measured by gel permeation chromatography (GPC), and the measurement conditions are as follows.
(Measurement Conditions)
Apparatus: "HLC-8120GPC" manufactured by Tosoh Corporation
Column: "TSKgel Super HM-M" manufactured by Tosoh Corporation
Detector: Differential refractive index detector (RI detector/built-in)
Solvent: Chloroform
Temperature: 40° C.
Flow Rate: 0.5 mL/min
Injection Volume: 20 μL
Concentration: 0.1% by weight
Calibration Material: Monodispersed polystyrene
Calibration Method: Polystyrene conversion
<Component (B)>

In the present invention, as described above, component (B) is a polypropylene resin containing "component (B1): modified polypropylene obtained by graft-modifying a polypropylene resin with a diene compound". Component (B) may contain "component (B2): polypropylene resin". Component (B2) does not include those corresponding to component (B1).
Polypropylene Resin In the present invention, the polypropylene resin used as a raw material of component (B1) is specifically a homopolymer, a block copolymer, a graft copolymer, and a random copolymer of propylene, and includes a crystalline polymer. A copolymer of propylene containing 75% by weight or more of propylene units is preferable in that crystallinity, rigidity, chemical resistance, and the like, which are characteristics of polypropylene, are maintained.

Examples of the monomer copolymerizable with the propylene constituting the propylene copolymer used as the raw material of component (B1) include α-olefins having 2 or 4~12 carbon atoms, such as ethylene, 1-butene, isobutene, 1-pentene, 3-methyl-1-butene, 1-hexene, 4-methyl-1-pentene, 3,4-dimethyl-1-butene, 1-heptene, 3-methyl-1-hexene, 1-octene, and 1-decene; cyclic olefins such as cyclopentene, norbornene, and tetracyclo [6,2,11,8,13,6]-4-dodecene; dienes such as 5-methylene-2-norbornene, 5-ethylidene-2-norbornene, 1,4-hexadiene, methyl-1,4-hexadiene, and 7-methyl-1,6-octadiene; and vinyl monomers such as vinyl chloride, vinylidene chloride, acrylonitrile, vinyl acetate, acrylic acid, methacrylic acid, maleic acid, ethyl acrylate, butyl acrylate, methyl methacrylate, maleic anhydride, styrene, methylstyrene, vinyltoluene, and divinylbenzene. These may be used alone or in a combination of two or more types. Among these, ethylene and 1-butene are preferable in that they are cheap and easy to handle.

Although the density of the polypropylene resin used as a raw material of component (B1) is not particularly limited, it is usually 0.87 g/cm$^3$ or more; and preferably 0.88 g/cm$^3$ or more, and normally 0.92 g/cm$^3$ or less; and preferably 0.91 g/cm$^3$ or less.

In the present invention, the polypropylene resin used as component (B2) is specifically a homopolymer of propylene, a block copolymer, a graft copolymer, or a random copolymer, and examples thereof include crystalline polymers. A copolymer of propylene containing 75% by weight or more of propylene units is preferable in that crystallinity, rigidity, chemical resistance, and the like, which are characteristics of polypropylene, are maintained.

Examples of the monomer copolymerizable with the propylene constituting the propylene copolymer used as the raw material of component (B2) include α-olefins having 2 or 4 to 12 carbon atoms, such as ethylene, 1-butene, isobutene, 1-pentene, 3-methyl-1-butene, 1-hexene, 4-methyl-1-pentene, 3,4-dimethyl-1-butene, 1-heptene, 3-methyl-1-hexene, 1-octene, and 1-decene; cyclic olefins such as cyclopentene, norbornene, and tetracyclo [6,2,11,8,13,6]-4-dodecene; dienes such as 5-methylene-2-norbornene, 5-ethylidene-2-norbornene 1,4-hexadiene, methyl-1,4-hexadiene, and 7-methyl-1,6-octadiene; and vinyl monomers such as vinyl chloride, vinylidene chloride, acrylonitrile, vinyl acetate, acrylic acid, methacrylic acid, rnaleic acid, ethyl acrylate, butyl acrylate, methyl methacrylate, maleic anhydride, styrene, methylstyrene, vinyltoluene, and divinylbenzene. These may be used alone or in a combination of two or more types. Among these, ethylene and 1-butene are preferable in that they are cheap and easy to handle.

Although the density of the polypropylene resin used as component (B2) is not particularly limited, it is usually 0.87 g/cm$^3$ or more; and preferably 0.88 g/cm$^3$ or more, and normally 0.92 g/cm$^3$ or less; and preferably 0.91 g/cm$^3$ or less.

The polypropylene resin used for component (B2) and the raw material of component (B1) may be used in a combination of two or more types of the above resin. Further, as component (B2) and the raw material of component (B1), different polypropylene resins may be used respectively, or the same resin may be used.

A stereoregularity of the polypropylene resin used for component (B2) and the raw material of component (B1) respectively is not particularly limited, but a propylene chain may be any of isotactic, syndiotactic, atactic, stereoblock, and the like, and the propylene chain is preferably isotactic, and particularly preferably an isotactic homopolypropylene. A catalyst used for polymerization and a well-known catalyst can be appropriately adopted.

Although in the present invention, a melt flow rate (MFR) of the polypropylene resin used for component (B2) and the raw material of component (B1) is not particularly limited, it is usually 0.5 g/10 min or more; preferably 1 g/10 min more; and more preferably 2 g/10 min or more, and usually 100 g/10 min or less; preferably 80 g/10 min or less; and more preferably 70 g/10 min or less under conditions of ISO 1133 (120° C., load 2.16 kg).

In a case where the MFR is smaller than a lower limit, a cohesive force alone may be strong and uniform miscibility with other components may be insufficient; an energy load at producing the thermoplastic elastomer composition used in the present invention may be too large; and a mold transferability when molding an elastomer composition composed of the thermoplastic elastomer composition may be poor and the liquid leakage sealing properties may deteriorate. In a case where the MFR is larger than the upper limit, the liquid leakage sealing properties and heat resistance of a medical member such as a medical container stopper and the like molded from the elastomer composition may deteriorate.

The polypropylene resin used for components (B1) and (B2) respectively can be obtained as a commercially available product. Examples of the polypropylene resin include "NOVA TEC (registered trademark) PP series", "WINTEC (registered trademark) series", "WELNEX (registered trademark) series", and the like manufactured by Japan Polypropylene Corporation, and the corresponding product can be appropriately selected and used among these.

<Component (B1)>

In the present invention, component (B1) is a modified polypropylene obtained by graft modifying the polypropylene resin with a diene compound. Examples of the diene compound which can be used herein include conjugated diene compounds such as butadiene, isoprene, 1,3-heptadiene, 2,3-dimethylbutadiene, and 2,5-dimethyl-2,4-hexadiene. These compounds may be used alone or in any combination and ratio of two or more types. Among these, butadiene and isoprene are preferable, and isoprene is particularly preferable.

Any kind of methods may be used for the modification for obtaining component (B1), and component (B1) can be manufactured by, for example, a method described in JP-A-2015-98542. Examples of the method include irradiating the polypropylene resin with radiation or melt-mixing the polypropylene resin, the diene compound, and a radical generating agent, Among these, the method of melt-mixing the polypropylene resin, the diene compound, and the radical generating agent is preferable from a viewpoint that the modified polypropylene can be manufactured at a low price without requiring expensive equipment.

Examples of an apparatus for reacting the polypropylene resin, the diene compound, and the radical generating agent include a kneading machine such as a roll, a ko-kneader, a Banbury mixer, a Brabender, a single-screw extruder and a twin-screw extruder, a horizontal stirrer such as, a 2-axis surface renewal machine, a 2-axial multi-disc device, and the like, and a vertical stirrer such as a double-helical ribbon stirrer. Among these, the kneader is, preferably used, and in particular, the extruder is preferable from a viewpoint of productivity.

The order and method of mixing, kneading (stirring) the polypropylene resin, the diene compound, and the radical generating agent are not particularly limited. The polypropylene resin, the diene compound and the radical generating agent may be mixed and then melt-kneaded (stirred); after melt-kneading (stirring) the polypropylene resin, the diene compound or the radical generating agent may be collectively or dividedly mixed simultaneously or separately; or after melt-kneading (stirring) either one of the polypropylene resin and the diene compound, and the radical generating agent, the other one of the diene compound and the radical generating agent may be added and melt-kneaded (stirred). It is preferable in that the temperature of the kneading (stirring) machine is 130° C. or higher and 300° C. or lower, but the polypropylene resin melts and does not thermally decompose. The kneading (stirring) time is preferably generally from 1 to 60 minutes.

The shape and size of the modified polypropylene thus obtained are not limited, and may be a pellet form.

Although the blending ratio of the diene compound to the polypropylene resin is not particularly limited, it is usually 0.01 part by weight or more; preferably 0.05 part by weight or more; more preferably 0.1 part by weight or more, and usually 30 parts by weight or less; preferably 10 parts by weight or less; and more preferably 5 parts by weight or less with respect to 100 parts by weight of the polypropylene resin.

A monomer copolymerizable with the diene compound such as vinyl chloride, vinylidene chloride, acrylonitrile, methacrylonitrile, acrylamide, methacrylamide, vinyl acetate, acrylic acid, methacrylic acid, maleic acid, maleic anhydride, metal salts of acrylic acid, metal salts of methacrylic acid, acrylic acid esters such as methyl acrylate, ethyl acrylate, butyl acrylate, 2-ethylhexyl acrylate, and stearyl actylate, and methacrylic acid esters such as methyl methacrylate, ethyl methacrylate, butyl methacrylate, 2-ethylhexyl methacrylate, stearyl methacrylate may be used alone or in a combination of two or more types with the diene compound.

Although the radical generating agent is not particularly limited, peroxides, azo compounds, or the like can be used. Specific examples include diacyl peroxides such, as diperoxide and dilauroyl peroxide, dialkyl peroxides such as dicumyl peroxide, tert-butyl cumyl peroxide, di-tert-butyl peroxide, 2,5-dimethyl-2,5-di(tert-butylperoxy) hexyne-3, α,α'-bis(tert-butylperoxy-m-isopropyl) benzene, and 2,5-dimethyl-2,5-di(tert-butylperoxy) hexane, alkyl peroxy esters such as tert-butyl peroxybenzoate, tert-butyl peroxyisobutyrate, tert-butyl peroxypivalate, and cumyl peroxypivalate, peroxycarbonates such as tert-butyl peroxy isopropyl carbonate, tert-butyl peroxy 2-ethylhexyl carbonate, tert-amyl peroxy isopropyl carbonate, peroxyketals such as 1,1-bis(tert-butylperoxy) 3,3,5-trimethylcyclohexane 1,1-bis(tert-butylperoxy) cyclohexane, n-butyl 4,4-bis(tert-butylperoxy) valerate, and 2,2-bis(tert-butylperoxy) butane, azo compounds such as azobisisobutyroninile and dimethylazoisobutyrate, and the like.

These radical generating agents can be appropriately selected depending on the type and MFR of the raw material polypropylene resin, the type and reaction conditions of the dime compound, and the like, and may be used alone, or may be used in any combination and ratio of two or more types.

Although the blending amount of the radical generating agent is not particularly limited, it is usually 0.001 to 20 parts by weight; preferably 0.005 to 10 parts by weight; more preferably 0.01 to 5 parts by weight; and particularly preferably 0.05 to 4 parts by weight with respect to 100 parts by weight of the polypropylene resin.

In the present invention, in component (B1), modified polypropylene corresponding to the above can also be used alone, and can also be used in any combination and ratio of two or more types.

Although the MFR (ISO 1133 (230° C., load 2.16 kg)) of component (B1) is not particularly limited, it is preferably in a range of 0.1 to 200 g/10 min. Namely, the MFR is preferably 0.1 g/10 min or more; more preferably 1 g/10 min or more; and still more preferably 3 g/10 min or more, and preferably 200 g/10 min or less; more preferably 170 g/10 min or less; and still more preferably 150 g/10 min or less.

<Blending Ratio of Component (B1) and Component (B2)>

It is arbitrary that component (B) contains component (B2), and the blending ratio of component (B1) and component (B2) is not particularly limited. In a case where component (B2) is used together with component (B1), the content of component (B1) is usually 1% by weight or more, preferably 5% by weight or more, and more preferably 10% by weight or more with respect to the total amount of components (B1) and (B2). The upper limit is not particularly limited, and is generally 100% by weight. By making the content of component (B1) equal to or greater than the lower limit, the liquid leakage sealing properties and heat resistance in the medical container stopper molded from the elastomer composition of the present invention are improved.

<Component (C)>

Component (C) used in the thermoplastic elastomer of the present invention is a hydrocarbon softener for rubber, Component (C) softens the elastomer composition, improves softness, elasticity, processability, and fluidity, and contributes to improvement of the external appearance and the like of the obtained molded body and improvement of balance between the liquid leakage sealing properties and the needle sticking properties in case of being molded into the medical container stopper.

Although examples of the hydrocarbon softener for rubber include a mineral oil-based softener, a synthetic resin-based softener, and a low-polymerization-degree vinyl polymer (olefin polymer, diene compound polymer, acrylic polymer, and the like) which is liquid at normal temperature (20° C.), and the like, a mineral oil-based softener and a synthetic resin-based softener are preferable from a viewpoint of affinity with other components. The mineral oil-based softener is generally a mixture of aromatic hydrocarbons, naphthenic hydrocarbons, and paraffinic hydrocarbons, those in which 50% or more of all carbon atoms belong to paraffinic hydrocarbons are called paraffinic oils, those in which 30%-45% of all carbon atoms belong to naphthenic hydrocarbons are called naphthenic oils, and those in which 35% or more of all carbon atoms belong to aromatic hydrocarbons are called aromatic oils. Among these, paraffin oils are preferably used in the present invention. The hydrocarbon softener for rubber may be used alone or in any combination and ratio of two or more types.

Although the kinematic viscosity of the hydrocarbon softener for rubber at 40° C. is not particularly limited, it is preferably 20 centistokes or more; and more preferably 50 centistokes or more, and is preferably 800 centistokes or less; and more preferably 600 centistokes or less. A flash point (COC method) of the hydrocarbon softener for rubber is preferably 200° C. or higher, and more preferably 250° C. or higher.

The hydrocarbon softener for rubber of component (C) can be obtained as a commercially available product. Examples of the corresponding commercially available product include "Nisseki polybutene (registered trademark) HV series" manufactured by JXTG Nippon Oil R. Energy Corporation, "Diana (registered trademark) process oil PW series" manufactured by Idemitsu Kosan Co., Ltd., "Lucant (registered trademark) series" manufactured by Mitsui Chemicals, and the like, and the corresponding product can be appropriately selected and used among these.

<Content of Each Component>

The thermoplastic elastomer composition of the present invention contains the component (A), component (B) and component (C) in a predetermined ratio.

First, the content of component (A) is 20 to 80 by weight with respect to a total amount of components (A) to (C). Namely, the lower limit is 20% by weight or more; preferably 25% by weight or more and more preferably 30% by weight or more, and the upper limit is 80% by weight or less; preferably 70% by weight or less; and more preferably 60% by weight or less. Since the content of component (A) is equal to or higher than the lower limit, the heat resistance of the thermoplastic elastomer is good, and when the content is equal to or lower than the upper limit, the content is preferable from a viewpoint of the liquid leakage sealing properties, needle sticking properties, and molding processability of the medical container stopper molded using the elastomer composition consisting of the thermoplastic elastomer composition.

The content of component (B) is 1 to 25% by weight wide respect to the total amount of components (A) to (C). Namely, the lower limit is 1% by weight or more; preferably 3% by weight or more; and more preferably 5% by weight or more, and the upper limit is 25% by weight or less; preferably 20% by weight or less; and more preferably 15% by weight or less. Since the content of component (B) is equal to or higher than the lower limit, the liquid leakage sealing properties and needle sticking properties of the medical container stopper are good, and when the content is equal to or lower than the upper limit value, the heat resistance of the thermoplastic elastomer composition is good.

The content of component (C) is 1 to 70% by weight with respect to the total amount of components (A) to (C). Namely, the lower limit is 1% by weight or more; preferably 10% by weight or more; and more preferably 15% by weight or more, and the upper limit is 70% by weight or less; preferably 60% by weight or less; and more preferably 55% by weight or less. Since the content of component (C) is equal to or higher than the lower limit, the content is preferable in terms of deterrence of blocking of the thermoplastic elastomer, and when the content is equal to or less than the upper limit, the content is preferable in view of the liquid leakage sealing properties and heat resistance of the medical container stopper. Since the content of component (C) is within the above range, the fluidity of the thermoplastic elastomer composition is not too high, and the fluidity is not too low, and the moldability is good.

<Other Components>

In addition to components (A) to (C), other components can be combined as necessary to the thermoplastic elastomer composition of the present invention in a scope of not impairing effects of the present invention.

Examples of other components include resins such as thermoplastic resins and elastomers other than component (A) and component (B), and various additives such as fillers, antioxidants, thermal stabilizers, light stabilizers, ultraviolet absorbents, neutralizes, lubricants, antifog additives, anti-blocking agents, dispersants, colorants, flame retardants, flame retardant aids, antistatic agents, conductivity imparting agents, metal deactivators, molecular weight modifiers, crystal nucleating agents, impact modifiers, pigments, compatibilizers, adhesion imparting agents, antibacterial agents, fungicides, and fluorescent brighteners. Any of these can be used alone or in a combination.

Examples of the thermoplastic resin other than component (A) and component (B) include polyphenylene ether resin, polyamide resins such as nylon 6, nylon 66, and nylon 11, polyester resins such as polyethylene terephthalate and polybutylene terephthalate, polyoxymethylene resins such as polyoxymethylene homopolymer and polyoxymethylene copolymer, and acrylic/metal acrylic resins such as polymethyl methacrylate resins, ethylene-vinyl acetate copolymers, polyurethane resins, polycarbonate resins, polyvinyl chloride resins, and polyolefin resins (however, except those corresponding to component (B)). Examples of the elastomer other than component (A) and component (B) include olefin elastomers such as ethylene-propylene copolymer rubber (EPM), ethylene-propylene-non-conjugated diene copolymer rubber (EPDM), ethylenebutene copolymer rubber (EBM), and ethylene-propylene-diene copolymer rubber, polyvinyl chloride elastomers and polybutadiene elastomers, and styrene elastomers such as styrene-butadiene copolymer rubber and styrene-isoprene copolymer rubber (however, except those corresponding to component (A)), and polyester elastomers, those modified with a hydrogenated product, an acid anhydride, and the like of the elastomers and introducing a polar functional group, those graft, random and/or block copolymerizing other monomers, and the like. These components may be used alone or in any combination and ratio of two or more types.

The filler is generally classified into organic fillers and inorganic fillers. Examples of the organic fillers include naturally derived polymers such as starch, cellulose fine particles, wood flour, tofu refuse, rice full, and wheat bran, modified products thereof and the like. Examples of the inorganic fillers include talc, calcium carbonate, zinc carbonate, wollastonite, silica, alumina, magnesium oxide, calcium silicate, sodium aluminate, calcium aluminate, sodium aluminosilicate, magnesium silicate, a glass balloon, carbon black, zinc oxide, antimony trioxide, zeolite, hydrotalcite, metal fiber, metal whisker, ceramic whisker, potassium titanate, boron nitride, graphite, carbon fiber, glass fiber, mica, metal soap, titanium dioxide, and the like. In a case where fillers are used, 0.1 to 50 parts by weight with respect to a total of 100 parts by weight of component (A) to component (C) are usually used.

Examples of the thermal stabilizer and the antioxidant include hindered phenols, phosphorus compounds, hindered amines, sulfur compounds, copper compounds, halides of alkali metals, and the like. In a case where the thermal stabilizer and the antioxidant are used, a range of 0.01 to 3 parts by weight with respect to a total of 100 parts by weight of component (A) to component (C) are usually used.

Examples of the lubricant include silicone oil, fatty acid amide, fatty acid glyceride, and the like. In a case where the lubricant is used, a range of 0.01 to 10 parts by weight with respect to a total of 100 parts by weight of component (A) to component (C) are usually used.

Even in a case where resins and components other than components (A) to (C) are used, a total amount of components (A) to (C) in the thermoplastic elastomer composition of the present invention is preferably 60% by weight, or more, and more preferably 80% by weight or more from a viewpoint of ease of finding excellent effects of the present invention. The upper limit here is usually 100% by weight.

<Method for Manufacturing Thermoplastic Elastomer Composition>

The thermoplastic elastomer composition of the present invention is manufactured by mixing the above components at a predetermined ratio.

The method for manufacturing the thermoplastic elastomer composition of the present invention is not particularly limited as long as the raw material components are uniformly dispersed. Namely, by mixing the raw material components and the like at the same time or in any order, a resin composition in which each component is uniformly distributed can be obtained.

The thermoplastic elastomer composition of the present invention also includes a state in which each of the raw material components is dry-blended as it is, and the thermoplastic elastomer composition may be used as the elastomer composition of the present invention as it is. However, it is preferable to melt-mix each of the raw material components for more uniform mixing and dispersion. As a method of melt mixing, for example, the raw material components and the like of the thermoplastic elastomer composition of the present invention may be mixed in any arbitrary order and then heated; or, may be mixed with sequentially melting all raw material components and the like, and a mixture of the raw material components or the like may be pelletized or melt-mixed at the time of molding when an object molded product is produced.

Although the mixing method and mixing conditions at mixing the raw material components are not particularly limited as long as the raw material components and the like are uniformly mixed, in terms of productivity, a well-known melt kneading method of a continuous kneading, machine such as a single-screw extruder and a twin-screw extruder, a batch type kneading machine such as a mill roll, a Banbury mixer, and a pressurized kneader, and the like is preferable. Although the temperature at the time of melt mixing may be any temperature at which at least one of the raw material components is in a molten state, a temperature at which all components usually used are melted is selected, which is generally in a grange of 150° C.~250° C.

<Properties of Elastomer Composition>

The elastomer composition of the present invention preferably has durometer hardness A of from 10 to 40 measured in accordance with ISO 7619-1. The durometer hardness A is preferably 40 or less, more preferably 38 or less, and even more preferably 36 or less. Further, the durometer hardness A is preferably 10 or more, more preferably 15 or more, and even more preferably 20 or more.

<Medical Member>

The molded body formed by molding the elastomer composition of the present invention can be suitably used as a medical member such as a medical container stopper.

<Method for Molding Medical Member>

The medical member of the present invention can be obtained by molding the elastomer composition of the present invention described above. Examples of the molding method which can be used include various molding methods such as a normal injection molding method, a compression molding method, an extrusion molding method, or as necessary, a gas injection molding method, an injection compression molding method, and a short shot molding method, and among these, injection molding or compression molding is preferable in consideration of a molding cycle and mass productivity.

<Applications and Properties of Medical Member>

The medical member of the present invention has small compression set, and is excellent in softness, liquid leakage sealing properties, needle sticking properties, sterilization stability, molding processability, and the like. Therefore, the medical member of the present invention more specifically can be suitably used as a medical container stopper of vials for liquid medicine, vials for powder preparations, vacuum blood collection tubes, transfusion bags, and the like; a medical cap of blood collection needle covers, syringes, and the like; a medical gasket of disposable syringes, prefilled syringes, and the like; a medical packing of O-rings; a catheter tube of transfusion, artificial dialysis, connection pipes, tourniquets, respiratory apparatuses, and the like; and a resuscitator of masks, bags, reservoirs, and the like. Among these, the medical member of the present invention can be particularly suitably used as a medical container stopper, and can be most suitably used as a medical rubber stopper.

In a case where the medical member of the present invention is a medical container stopper used in a medical container such as an transfusion bag, the shape of the medical container stopper is not limited, but generally includes a truncated cone shape, a cylindrical shape, a disc shape, or the like, and the diameter thereof is usually about from 10 mm to 20 mm. Although the thickness of the medical container stopper (thickness in a direction of piercing the injection needle) is not limited, it is usually about from 4 mm to 8 mm. In general, a stopper body made of the thermoplastic elastomer used for an transfusion bag should be thickened to ensure liquid leakage sealing properties, and cannot be thickened from a viewpoint of piercing properties. However, since the liquid leakage sealing properties and needle sticking properties are good, the medical container stopper of the present invention can be suitably used for the transfusion bag even in a case where the thickness is 8 mm or more.

The present invention also includes the following configurations (1) to (6). (1) A medical member containing the thermoplastic elastomer composition containing 20 to 80% by weight of component (A), 1 to 25% by weight of component (B), and 1 to 70% by weight of component (C) with respect to a total amount of the following component (A), component (B), and component (C):

Component (A): at least one block copolymer selected from: a block copolymer having a polymer block derived from a vinyl aromatic compound and a polymer block derived from conjugated diene and/or isobutylene; and a block copolymer obtained by hydrogenating the block copolymer;

Component (B): a polypropylene resin containing component (B1) below

Component (B1): a modified polypropylene obtained by graft-modifying a polypropylene resin with a conjugated diene compound; and Component (C): a hydrocarbon softener for rubber.
(2) The medical member according to the above (1), in which a conjugated diene compound of the component (B1) is isoprene.
(3) The medical member according to the above (1) or (2), in which the component (B1) has a melt flow rate (ISO 1133 (230° C., load 2.16 kg)) of 0.1 to 200 g/10 min.
(4) The medical member according to any one of the above (1) to (3), in which the weight average molecular weight (Mw) of the component (A) is 100,000-500,000.
(5) The medical member according to any one of the above (1) to (4), in which the durometer hardness (ISO 7619-1) of the thermoplastic elastomer composition is 10-40.
(6) The medical m according to any one of the above to (5) which is a medical rubber stopper.

EXAMPLES

Hereinafter, although specific embodiments of the present invention will be described in more detail using Examples, the present invention is not limited to the following Examples unless the present invention does not exceed the gist. Values various production conditions and evaluation results in the following Examples having meanings as preferable values of the upper limit or the lower limit in embodiments of the present invention, and a preferable range may be a range defined by a combination of a value of the upper limit or the lower limit and values of the following Examples or values of Examples.
[Raw Materials]

Materials used in Examples and Comparative Examples are shown below.
(Component (A))
A-1: "Septon (registered trademark) J3341" manufactured by Kuraray Co., Ltd. (hydrogenated product of styrene-isoprene-butadiene-styrene block copolymer) [weight average molecular weight (Mw): 340,000, styrene content: 40% by weight]
A-2: "Hybrar (registered trademark) 7135" manufactured by Kuraray Co., Ltd. (hydrogenated product of styrene-isoprene-styrene block copolymer) [weight average molecular weight (Mw): 280,000, styrene content: 33% by weight]
A-3: "Septon (registered trademark) 4055" manufactured by Kuraray Co., Ltd. (hydrogenated product of styrene-isoprene-butadiene-styrene block copolymer) [weight average molecular weight (Mw): 290,000, styrene content: 30% by weight]
A-4: "Kraton (registered trademark) G1651HU" manufactured by Kraton Polymer Co nation (hydrogenated product of styrene-butadiene-styrene block copolymer) [weight average molecular weight (Mw): 250,000, styrene content: 33% by weight]
(Component (B))
<(Component (B1)>
B1-1: Isoprene graft-modified polypropylene manufactured by KANEKA Corporation (modified polypropylene obtained by grafting isoprene to a polypropylene homopolymer) [MFR (ISO 1133 (230° C., load 2.16 kg)): 56 g/10 min]
B1-2: Isoprene graft-modified polypropylene manufactured by KANEKA Corporation (modified polypropylene obtained by grafting isopene to a polypropylene homopolymer) [MFR (ISO 1133 (230° C., load 2.16 kg)): 20 g/10 min]
B1-3: Isoprene graft-modified polypropylene manufactured by KANEKA Corporation (modified polypropylene obtained by grafting isoprene to a polypropylene homopolymer [MFR (ISO 1133 (230° C., load 2.16 kg)): 100 g/10 min]
B1-4: Isoprene graft-modified polypropylene manufactured by KANEKA Corporation (modified polypropylene obtained by grafting isoprene to a polypropylene homopolymer) [MRF (ISO 1133 (230° C., load 2.16 kg)): 7 g/10 min]
B1-5: Isoprene graft-modified polypropylene manufactured by KANEKA Corporation (modified polypropylene obtained by grafting isoprene to a polypropylene-ethylene random polymer [MFR (ISO 1133 (230° C., load 2.16 kg)): 7 g/10 min]
<Component (B2)>
B2-1: "Novatec (registered trademark) PP FA3KM" manufactured by Japan Polypropylene Corporation (polypropylene homopolymer [MFR (ISO 1133 (230° C., load 2.16 kg)): 10 g/10 min])
B2-2: "Novatec (registered trademark) PP BC06AH" manufactured by Japan Polypropylene Corporation (polypropylene-ethylene block copolymer [MFR (ISO 1133 (230° C., load 2.16 kg)): 60 g/10 min])
Component (C))
C-1: "Diana (registered trademark) process oil PW90" (paraffinic oil) manufactured by Idemitsu Kosan Co., Ltd.
(Other Components)
d-1: "Irganox (registered trademark) 1330" (hindered phenol antioxidant) manufactured by BASF Japan Ltd.
e-1: "SH200-100CS" (silicone oil) [kinematic viscosity (25° C.): 100 cSt], manufactured by Dow Corning Toray Co., Ltd.

Examples 1 to 8 and Comparative Examples 1 and 2

Each raw material shown in Table 1 was charged into a twin-screw extruder ("TEM-26SS" manufactured by Toshiba Machine Co., Ltd., cylinder aperture: 26 mm) at a rate of 20 kg/hr, and the temperature was raised in a range of from 180° C. to 240° C. to perform melt kneading, thereby producing the elastomer composition. The obtained elastomer composition was molded into a sheet shape with using an injection molding machine ("IS130GN-5A" manufactured by Toshiba Machine Co., Ltd.). The injection molding conditions were ranges of resin temperature of from 180° C. to 240° C., injection time of from 2 to 20 seconds, mold temperature of from, 20° C. to 60° C., and cooling time of from 10 to 50 seconds. The following evaluations (1) to (3) were evaluated with using the obtained injection molded sheet (thickness 2 mm). The evaluation results are shown in Table 1.

(Evaluation Method)

A rubber stopper performance evaluation method using the elastomer composition is as follows.

(1) Softness (Durometer Hardness A)

The hardness (type A durometer) was measured based on ISO 7619-1. In order to be used as a rubber stopper, the durometer hardness A is preferably 10 or more and 40 or less from a viewpoint of reaction force during puncturing and re-sealing properties after puncturing.

(2) Compression Set

Compression set was measured based on ISO 815. The compression set is preferably 45% or less from a viewpoint of shape retention after heating sterilization.

(3) Evaluation of Medical Rubber Stopper Performance

In this evaluation, properties required for the medical rubber stopper were evaluated by the following method.

<Evaluation of Needle Sticking Properties>

A test piece having a diameter of 28 mm was punched using an injection molded sheet and attached to the jig shown in FIG. 1. Next, the maximum load (piercing resistance) that the medical plastic needle (TK-U200L manufactured by Terumo Corporation) 2 is inserted into the test piece 3 at a rate of 200 mm/min until pierced (the plastic needle 2 penetrates the test piece 3) and the displacement amount (piercing elongation) were measured with using an autograph. Three measurements were performed, an average value thereof was determined, and the value was evaluated according to the following evaluation criteria.

[Evaluation Criteria]

◉: Piercing resistance is 30 N or less and piercing elongation is 15 mm or less

○: Piercing resistance is 40 N or less and piercing elongation is 20 mm or less, which docs not correspond to criteria of "◉"

x: Piercing resistance is 40 N or more, or piercing elongation is 20 mm or more, which does not correspond to criteria of "○"

<Evaluation of Liquid Leakage Sealing Properties>

A test piece having a diameter of 18 mm was punched using an injection molded sheet and attached to a mouth stopper of a PET bottle for 500 mL of a commercially available beverage filled with 500 mL of disinfection ethanol ("disinfection ethanol IPA" manufactured by KENEI Pharmaceutical Co., Ltd.) A dedicated jig was attached to the mouth stopper such that there was no liquid leakage between the test piece and the PET bottle, and the PET bottle was installed upright. Next, a medical plastic needle (TK-U200L manufactured by Terumo Corporation) was manually inserted into the test piece from the vertically above. In this state, the PET bottle was left for 24 hours, and inverted immediately after the plastic needle was pulled out. Additionally, it was confirmed whether continuous dropping occurred, and the amount of water (liquid leakage amount) dropped in 40 seconds was measured. It is desirable that the amount of liquid leakage is small without continuous dropping, and it is more desirable that the amount of liquid leakage is less than one drop (0.05 g).

Three measurements were performed; an average value thereof was determined; and the value was evaluated according to the following evaluation criteria.

[Evaluation Criteria]

◉: no continuous dropping and a liquid leakage amount is less than 0.05 g

○: no continuous dropping and a liquid leakage amount is 0.05 g or more and less than 0.10 g x: continuously dropping by one or more test pieces, or a liquid leakage amount is 0.10 g or more

TABLE 1

| | | | Examples | | | | | | | | Comparative Examples | |
|---|---|---|---|---|---|---|---|---|---|---|---|---|
| | | | 1 | 2 | 3 | 4 | 5 | 6 | 7 | 8 | 1 | 2 |
| Blending composition [parts by weight] | Component (A) | A-1 | 36.8 | 36.8 | 36.8 | 36.8 | 36.8 | — | — | — | 36.8 | — |
| | | A-2 | — | — | — | — | — | 36.8 | — | — | — | — |
| | | A-3 | — | — | — | — | — | — | 36.8 | — | — | 30 |
| | | A-4 | — | — | — | — | — | — | — | 36.8 | — | — |
| | Component (B) | Component (B1) | B1-1 | 8 | — | — | — | — | — | — | — | — | 20 |
| | | B1-2 | — | 8 | — | — | — | 8 | 8 | — | — | — |
| | | B1-3 | — | — | 8 | — | — | — | — | — | — | — |
| | | B1-4 | — | — | — | 8 | — | — | — | — | — | — |
| | | B1-5 | — | — | — | — | 8 | — | — | — | — | — |
| | Component (B2) | B2-1 | — | — | — | — | — | — | — | — | 8 | — |
| | | B2-2 | — | — | — | — | — | — | — | — | — | 10 |
| | Component (C) | C-1 | 55.2 | 55.2 | 55.2 | 55.2 | 55.2 | 55.2 | 55.2 | 55.2 | 55.2 | 40 |
| | Component (d) | d-1 | 0.05 | 0.05 | 0.05 | 0.05 | 0.05 | 0.05 | 0.05 | 0.05 | 0.05 | 0.05 |
| | Component (e) | e-1 | 0.05 | 0.05 | 0.05 | 0.05 | 0.05 | 0.05 | 0.05 | 0.05 | 0.05 | 0.05 |
| Evaluation | Durometer hardness A | — | 29.7 | 32.1 | 28.2 | 32.8 | 29.4 | 20.5 | 34.9 | 32.3 | 29.5 | 82.9 |
| | Compression set | % | 39.4 | 40.4 | 40.4 | 42.3 | 42.9 | 28.1 | 37.4 | 31.5 | 48.6 | 54.2 |
| | Needle sticking properties | Maximum load Kgf | 18.5 | 18.4 | 18.1 | 18.9 | 19.7 | 20.8 | 33.6 | 36.5 | 17.5 | 43.4 |
| | | Displacement amount mm | 13.2 | 12.2 | 13.6 | 12.0 | 12.6 | 14.3 | 18.3 | 18.8 | 12.5 | 8.6 |
| | | Evaluation | ◎ | ◎ | ◎ | ◎ | ◎ | ◎ | ○ | ○ | ◎ | × |
| | Liquid leakage properties | Liquid leakage amount mL | 0.01 | 0.03 | 0.01 | 0.05 | 0.02 | 0.03 | 0.01 | 0.03 | 0.13 | 6.14 |
| | | Number of tests without continuous dropping number | 3 | 3 | 3 | 3 | 3 | 3 | 3 | 3 | 1 | 0 |
| | | Number of tests with continuous dropping number | 0 | 0 | 0 | 0 | 0 | 0 | 0 | 0 | 2 | 3 |
| | | Evaluation | ◎ | ◎ | ◎ | ○ | ◎ | ◎ | ◎ | ◎ | × | × |

※In the table "—" in the blending composition indicates that the components are not blended From Table 1, it is known that the rubber stopper made from the elastomer composition of the present invention containing, component (A), component (B), and component (C) at a predetermined ratio has small compression set, and is excellent in softness, liquid leakage sealing properties, and needle sticking properties.

In contrast, in Comparative Example 1 which does not contain component (B1) as component (B), the compression set is large and the liquid leakage sealing properties are inferior.

In Comparative Example 2 in which the content of component (B1) is too high, the compression set is larger, and the needle sticking properties and liquid leakage sealing properties remarkably decrease.

While the present invention has been described in detail with reference to specific embodiments, it is apparent to those skilled in the art that various changes and modifications can be made without departing from the spirit and scope of the present invention. This application is based on Japanese Patent Application 2016-041123 on filed Mar. 3, 2016, the contents of which are incorporated herein by reference.

DESCRIPTION OF REFERENCE NUMERALS

1: jig for evaluating needle sticking properties
2: plastic needle
3: test piece

The invention claimed is:

1. A medical member, comprising an elastomer composition comprising a thermoplastic elastomer composition comprising 20 to 80% by weight of component (A), 1 to 25% by weight of component (B), and 1 to 70% by weight of component (C) with respect to a total amount of the following component (A), component (B), and component (C):
Component (A): at least one block copolymer selected from: a block copolymer having a polymer block derived from a vinyl aromatic compound and a polymer block derived from at least one selected from a conjugated diene and isobutylene; and a block copolymer obtained by hydrogenating the block copolymer;
Component (B): a polypropylene resin containing component (B1) below
Component (B1): a modified polypropylene obtained by graft-modifying a polypropylene resin with a diene compound; and
Component (C): a hydrocarbon softener for rubber,
wherein the elastomer composition has durometer hardness A (ISO 7619-1) of 10 to 40.

2. The medical member according to claim 1, wherein the diene compound of the component (B1) is a conjugated diene compound.

3. The medical member according to claim 2, wherein the conjugated diene compound of the component (B1) is isoprene.

4. The medical member according to claim 1, wherein the component (1) has a melt flow rate (ISO 1133 (230° C., load 2.16 kg)) of 0.1 to 200 g/10 min.

5. The medical member according to claim 1, wherein a weight average molecular weight (Mw) of the component (A) is 100,000 to 500,000.

6. A medical container stopper, comprising an elastomer composition comprising a thermoplastic elastomer composition comprising 20 to 80% by weight of component (A), 1 to 25% by weight of component (B), and 1 to 70% by weight of component (C) with respect to a total amount of the following component (A), component (B), and component (C):
Component (A): at least one block copolymer selected from: a block copolymer having a polymer block derived from a vinyl aromatic compound and a polymer block derived from at least one selected from a conjugated diene and isobutylene; and a block copolymer obtained by hydrogenating the block copolymer;
Component (B): a polypropylene resin containing component (B1) below
Component (B1): a modified polypropylene obtained by graft-modifying a polypropylene resin with a diene compound; and
Component (C): a hydrocarbon softener for rubber.

7. The medical container stopper according to claim 6, which is a medical rubber stopper.

8. The medical container stopper according to claim 6, wherein the diene compound of the component (B1) is a conjugated diene compound.

9. The medical container stopper according to claim 8, wherein the conjugated diene compound of the component (B1) is isoprene.

10. He medical container stopper according to claim 6, wherein the component (B1) has a melt flow rate (ISO 1133 (230° C., load 2.16 kg)) of 0.1 to 200 g/10 min.

11. The medical container stopper according to claim 6, wherein a weight average molecular weight (Mw) of the component (A) is 100,000 to 500,000.

12. The medical container stopper according to claim 7, wherein the diene compound of the component (B1) is a conjugated diene compound.

13. The medical container stopper according to claim 12, wherein the conjugated diene compound of the component (B1) is isoprene.

14. The medical container stopper according to claim 7, wherein the component (B1) has a melt flow rate (ISO 1133 (230° C., load 2.16 kg)) of 0.1 to 200 g/10 min.

15. The medical container stopper according to claim 7, wherein a weight average molecular weight (Mw) of the component (A) is 100,000 to 500,000.

* * * * *